US012797055B2

(12) United States Patent
Ali

(10) Patent No.: US 12,797,055 B2

(45) Date of Patent: Nov. 17, 2026

(54) VACUUM ASSISTED OCCLUSION OF THE LEFT ATRIAL APPENDAGE

(71) Applicant: Muhammad Ali, Braunschweig (DE)

(72) Inventor: Muhammad Ali, Braunschweig (DE)

( * ) Notice: Subject to any disclaimer, the term of this patent is extended or adjusted under 35 U.S.C. 154(b) by 8 days.

(21) Appl. No.: 19/538,061

(22) Filed: Feb. 12, 2026

(65) Prior Publication Data

US 2026/0157738 A1 Jun. 11, 2026

Related U.S. Application Data

(63) Continuation-in-part of application No. 19/241,649, filed on Jun. 18, 2025, now Pat. No. 12,594,079.

(60) Provisional application No. 63/664,848, filed on Jun. 27, 2024.

(51) Int. Cl.
*A61B 17/00* (2006.01)

(52) U.S. Cl.
CPC .... *A61B 17/0057* (2013.01); *A61B 17/00234* (2013.01); *A61B 2017/00243* (2013.01); *A61B 2017/00305* (2013.01); *A61B 2017/00367* (2013.01); *A61B 2017/00544* (2013.01); *A61B 2017/00566* (2013.01); *A61B 2017/00632* (2013.01); *A61B 2017/00867* (2013.01)

(58) Field of Classification Search
CPC .... A61B 2017/00561; A61B 17/12122; A61B 17/12031; A61B 17/12131
See application file for complete search history.

(56) References Cited

U.S. PATENT DOCUMENTS

| | | | |
|---|---|---|---|
| 5,938,645 | A | 8/1999 | Gordon |
| 6,152,144 | A | 11/2000 | Lesh et al. |
| 8,784,469 | B2 | 7/2014 | Kassab |
| 9,717,488 | B2 | 8/2017 | Kassab |
| 10,292,689 | B2 | 5/2019 | Sternik |
| 10,499,924 | B2 | 12/2019 | Kassab |
| 10,702,274 | B2 | 7/2020 | Groothuis et al. |
| 11,013,523 | B2 | 5/2021 | Arad Hadar |
| 11,266,389 | B2 | 3/2022 | Sternik |
| 11,793,542 | B2 | 10/2023 | Pons |

(Continued)

OTHER PUBLICATIONS

Tanyildizi, et al., "In vitro testing of a funnel-shaped tip catheter model to decrease clot migration during mechanical thrombectomy", Scientific Reports, 2020, 10:633, https://doi.org/10.1038/s41598-019-57315-9, (7 pages).

(Continued)

*Primary Examiner* — Christina C Lauer

(74) *Attorney, Agent, or Firm* — Ronald J. Richter; Nesbitt IP LLC

(57) ABSTRACT

An aspiration catheter and method of use for inverting the left atrial appendage (LAA) of a patient's heart. The aspiration catheter can include a proximal portion for attachment to a negative pressure source, and a distal portion for making suction contact with the interior wall of the LAA. The distal portion is preferably in the form of a self-expanding suction cup adapted to transition between a collapsed state and an expanded state. The proximal and distal portions share a common internal lumen for transmitting externally applied negative pressure therethrough, and the suction contact created by the negative pressure can adhere the suction cup portion of the catheter to the interior LAA wall for pulling or inverting the LAA into the left atrium.

11 Claims, 10 Drawing Sheets

(56) References Cited

U.S. PATENT DOCUMENTS

| | | | |
|---|---|---|---|
| 11,839,725 B2 | 12/2023 | Casey et al. | |
| 11,844,566 B2 | 12/2023 | Fung et al. | |
| 11,986,195 B2 | 5/2024 | Cortinas Villazon et al. | |
| 2003/0078473 A1 | 4/2003 | Richardson | |
| 2005/0021016 A1* | 1/2005 | Malecki | A61B 18/1492 606/27 |
| 2009/0182326 A1* | 7/2009 | Zenati | A61B 17/12013 606/41 |
| 2010/0324588 A1 | 12/2010 | Miles et al. | |
| 2011/0178539 A1 | 7/2011 | Holmes, Jr. et al. | |
| 2019/0298382 A1* | 10/2019 | Fung | A61B 17/12013 |
| 2019/0336136 A1 | 11/2019 | Kassab | |
| 2021/0186547 A1* | 6/2021 | Kassab | A61M 25/008 |
| 2023/0074249 A1 | 3/2023 | Smith et al. | |
| 2023/0389932 A1 | 12/2023 | Ozenne et al. | |
| 2025/0072900 A1* | 3/2025 | Berger | A61B 17/12013 |
| 2025/0134527 A1 | 5/2025 | Stoppenhagen et al. | |

OTHER PUBLICATIONS

Price, et al., "Left Atrial Appendage Closure to Prevent Stroke in Patients With Atrial Fibrillation", New Drugs and Technologies, Circulation. 2014;130:202-212, Jul. 8, 2014, (11 pages).

Vainrib, et al., Left Atrial Appendage Occlusion/Exclusion: Procedural Image Guidance with Transesophageal Echocardiography, Journal of American Society of Echocardiography, Apr. 2018, vol. 31, No. 4, pp. 454-474 (21 pages).

Miki, et al., "Clinical Significance of the Left Atrial Appendage Orifice Area", Internal Medicine, The Japanese Society of Internal Medicine, 61, 2022, pp. 1801-1807 (7 pages).

Zhuo, et al, "Impact of left atrial appendage orifice diameter on the safety and efficacy of left atrial appendage closure using the LAmbre device", Journal of the Formosan Medical Association, 123, 2024, pp. 600-605 (6 pages).

Sławek-Szmyt, et al, "Catheter-directed mechanical aspiration thrombectomy in a real-world pulmonary embolism population: a multicenter registry", European Society of Cardiology, European Heart Journal, 2023, 12, pp. 584-593 (10 pages).

Akinapelli, et al., "Left Atrial Appendage Closure—The WATCHMAN Device", Current Cardiology Reviews, 2015, vol. 11, No. 4, pp. 334-340 (7 pages).

Vella, et al., "Left atrial appendage inversion: First computational study to shed light on the phenomenon", Heliyon, 10, 2024, e26629, (9 pages).

Pasta, et al., "Inversion of Left Atrial Appendage Will Cause Compressive Stresses in the Tissue: Simulation Study of Potential Therapy", Journal of Personalized Medicine, 2022, 12, 883, (10 pages).

Sulkin, et al., "Suction catheter for enhanced control and accuracy of transseptal access", Clinical Research, Interventions for Valvular Disease and Heart Failure, 2016, 12, pp. 1534-1541 (8 pages).

* cited by examiner

VACUUM ASSISTED OCCLUSION OF THE LEFT ATRIAL APPENDAGE

CROSS REFERENCES TO RELATED APPLICATION

The present application is a continuation-in-part of U.S. application Ser. No. 19/241,649 filed Jun. 18, 2025, which claims the benefit of U.S. Provisional Application No. 63/664,848 filed Jun. 27, 2024, the disclosures of which are incorporated herein by reference in their entirety.

FIELD OF THE INVENTION

The present invention generally relates to medical/surgical devices and methods, and in particular to a device and method for use in occluding the left atrial appendage of the heart of a patient suffering from long-term atrial fibrillation.

BACKGROUND OF THE INVENTION

The left atrial appendage (LAA) is a normal part of the cardiac anatomy, presenting as a small pouch-like structure projecting from the anterolateral portion of the left atrial muscle wall. While its precise function is not fully understood, in patients with a normal sinus heart rhythm the LAA contracts rhythmically with the rest of the left atrium. It can act as a decompression chamber, receiving a larger volume of blood when atrial pressure is high, serving as a reservoir during atrial contraction, and assisting with filling of the left ventricle. However, in patients suffering from atrial fibrillation the LAA may not properly contract or empty all of its blood into the left atrium, causing stagnant blood to pool within its interior. This can lead to the undesirable formation of thrombi or blood clots within the LAA.

Atrial fibrillation (AFib) is an irregular and rapid heart rhythm, or arrhythmia, in which the upper chambers (i.e., the atria) of the heart function chaotically and irregularly, out of sync with the lower heart chambers (i.e., the ventricles). In a fibrillating atrium, the LAA becomes a major site of blood stasis, which significantly increases the risk of clot formation. AFib may initially have no symptoms, and usually is not a life-threatening heart problem. But if untreated, over time AFib can progress to intense periods of pounding and racing heartbeats, shortness of breath, light-headedness, and anxiety. Long-term AFib typically leads to a significantly increased risk of blood clots, or thrombi, being formed and released from the heart. Thrombi can migrate through the blood vessels and eventually plug smaller vessels downstream, thereby causing the patient to suffer an embolic stroke, pulmonary embolism, heart failure, or other complications.

Clinical echocardiography and autopsy studies have shown that the majority of blood clots in patients with atrial fibrillation originate in the left atrial appendage. Indeed, over 90% of thrombi found in patients with AFib and stroke are located in the LAA. As a result, patients diagnosed with AFib and its related risk for thromboembolic stroke are typically treated with long-term oral anticoagulants (OACs) in an attempt to prevent such complications. For most patients, the benefit from anticoagulation outweighs the associated increase in the risk of bleeding. However, major challenges to long-term therapy include a substantial hazard of major bleeding, and other side effects such as gastrointestinal issues and skin reactions. Noncompliance with long-term anticoagulant therapy is also a problem, due to the need for frequent monitoring and dose adjustments, and ongoing patient concerns about bleeding complications.

For patients who are unable to safely take long-term blood thinners or OACs, their best option may be to close off the LAA pouch. As a result, several medical devices, such as the AtriClip™ and the Watchman™ devices have been developed to be inserted for blocking or closing off the left appendage from the circulatory system. While such prior art devices may have certain advantages and disadvantages, they can also present a number of potential problems. For example, current surgical LAA closure procedures typically involve implanting an external device in the LAA to block the opening and prevent clots from entering the bloodstream, as well as stents, needles, clips, or other items. Implanting such devices in the heart can create a risk of dislodgement or migration of the implanted items, as well as incomplete wound closure, bleeding and blood clot formation, pericardial effusion, and infection.

For the above reasons, it would be desirable to provide a means to prevent thrombus formation in the LAA of AFib patients without having to implant a closure device into the LAA. It would also be useful to provide a device and method for inverting the LAA without stitching, sewing or clipping of the heart tissue.

SUMMARY OF THE INVENTION

Accordingly, the present invention relates to a device and method for inverting the left atrial appendage. The invention includes using a modified aspiration catheter to create suction contact with the interior wall of the LAA to pull it at least partially inside out, thereby decreasing the chances of thrombus formation in a patient suffering from atrial fibrillation.

A first aspect of the invention provides an aspiration catheter for inverting the left atrial appendage (LAA) of a patient's heart, the aspiration catheter comprising: a proximal portion for attachment to a negative pressure source; and a distal portion for making suction contact with the interior wall of the LAA, wherein the proximal and distal portions share a common internal lumen for transmitting externally applied negative pressure therethrough, and wherein said suction contact adheres the distal portion to the interior LAA wall.

A second aspect of the invention provides a system for inverting the left atrial appendage (LAA) of a patient's heart, the system comprising: an aspiration catheter for maneuvering through a patient's vasculature and into the left atrium, the catheter having an internal lumen therethrough for transmission of negative pressure, the aspiration catheter comprising: a proximal portion for attachment to a negative pressure source; and a distal portion for making suction contact with the interior wall of the LAA, wherein said suction contact adheres the distal portion to the interior LAA wall; a delivery sheath having an aperture therethrough for housing the aspiration catheter during maneuvering through the vasculature and heart and into the left atrium; and a negative pressure source coupled to the proximal portion of the catheter for transmitting negative pressure to the distal portion.

A third aspect of the invention provides a method for inverting the left atrial appendage (LAA) of a patient's heart, the method comprising the steps of: providing an aspiration catheter for maneuvering through a patient's vasculature and into the left atrium, the aspiration catheter comprising: (i) a proximal portion for attachment to a negative pressure source; and (ii) a distal portion for making suction contact with the interior wall of the LAA, wherein the distal portion is a self-expanding suction cup adapted to transition between a collapsed state and an expanded state, wherein the proximal and distal portions share a common internal lumen for transmitting externally applied negative pressure therethrough, and wherein said suction contact adheres the distal portion to the interior LAA wall; maneuvering the catheter with the distal portion in the collapsed state through a patient's vasculature and heart and into the left atrium of the heart; maneuvering the distal portion of the catheter past the ostium of the LAA; allowing the distal portion to self-expand to the expanded state within the LAA; attaching the proximal portion of the catheter to a vacuum device; activating the vacuum device for transmission of negative pressure to the distal portion; making suction contact between the distal portion and the interior LAA wall; withdrawing the aspiration catheter to cause the LAA pouch to invert, wherein a portion of the interior LAA wall is pulled through the LAA ostium and into the left atrium; and deactivating the vacuum device so that suction contact is broken and the distal portion detaches from the LAA wall.

Another aspect of the invention provides a self-expanding, radially torsional suction cup that is connectable to a distal end of a torqueable aspiration catheter shaft, the torqueable aspiration catheter shaft including a proximal end attached to a torque handle, wherein the suction cup connects to the distal end of the aspiration catheter shaft and is responsive to rotation of the torque handle to cause radial contraction and a progressive reduction in the diameter and length of the suction cup, wherein removal of the torsion created at the torque handle allows the suction cup to radially re-expand.

Another aspect of the invention provides an aspiration catheter for inverting a left atrial appendage (LAA), the aspiration catheter comprising: (a) a proximal portion for attachment to a negative pressure source, the proximal portion including a torque handle at the proximal end and a torqueable catheter shaft connected to the torque handle; and (b) a distal portion consisting of a self-expanding, radially torsional suction cup comprising a braided nitinol mesh structure in the form of radial struts that are torsion-responsive to rotation of the torque handle to cause radial contraction and a progressive reduction in the diameter and length of the suction cup, wherein the proximal and distal portions share a common internal lumen for transmitting externally applied negative pressure therethrough, wherein the suction cup is adapted for pulling the LAA through the LAA ostium into an inverted hat configuration, wherein the expanded suction cup is caused to radially collapse around, compress, and stabilize the LAA in the inverted hat configuration in response to torsion created at the proximal torque handle, wherein release of the torsion created at the proximal torque handle allows the suction cup to radially re-expand and controllably release from the inverted LAA so that the LAA remains in the inverted hat configuration without the need to implant a closure device.

Another aspect of the invention provides a method for inverting the left atrial appendage (LAA) of a patient's heart, the method comprising the steps of: (a) providing an aspiration catheter for maneuvering through a patient's vasculature and into the left atrium, the aspiration catheter comprising: (i) a proximal portion for attachment to a negative pressure source, the proximal portion comprising a torque handle and a torqueable aspiration catheter shaft; and (ii) a distal portion comprising a self-expanding, radially torsional suction cup connectable to the torqueable aspiration catheter shaft for making suction contact with an interior wall of the LAA, wherein the suction cup is responsive to rotation of the torque handle to cause radial contraction and a progressive reduction in the diameter and length of the suction cup, and wherein removing the torsion applied at the torque handle allows the suction cup to radially re-expand; (b) maneuvering the torqueable catheter shaft through a patient's vasculature and heart and into the left atrium of the heart; (c) maneuvering the suction cup past the ostium of the LAA; (d) allowing the suction cup to self-expand within the LAA; (e) attaching the aspiration catheter to an external suction device; (f) activating the external suction device for transmission of negative pressure to the suction cup; (g) making suction contact between the suction cup and the interior LAA wall; (h) capturing the interior LAA wall within the suction cup; (i) withdrawing the aspiration catheter, thereby pulling suction cup and the LAA through the LAA ostium and into the left atrium to cause the LAA to assume an inverted hat configuration; (j) creating a torsional force at the proximal torque handle to cause the suction cup to radially collapse around, compress, and stabilize the LAA in the inverted hat configuration; (k) removing the torsional force created at the proximal torque handle to allow the suction cup to radially re-expand and controllably release the suction cup from the inverted LAA; and (l) deactivating the external suction device to remove any remaining suction contact between the suction cup and the interior LAA wall, thereby maintaining the LAA in the inverted hat configuration without the need to implant a closure device.

The nature and advantages of the present invention will be more fully appreciated from the following drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

DETAILED DESCRIPTION OF THE INVENTION

Figure 1:
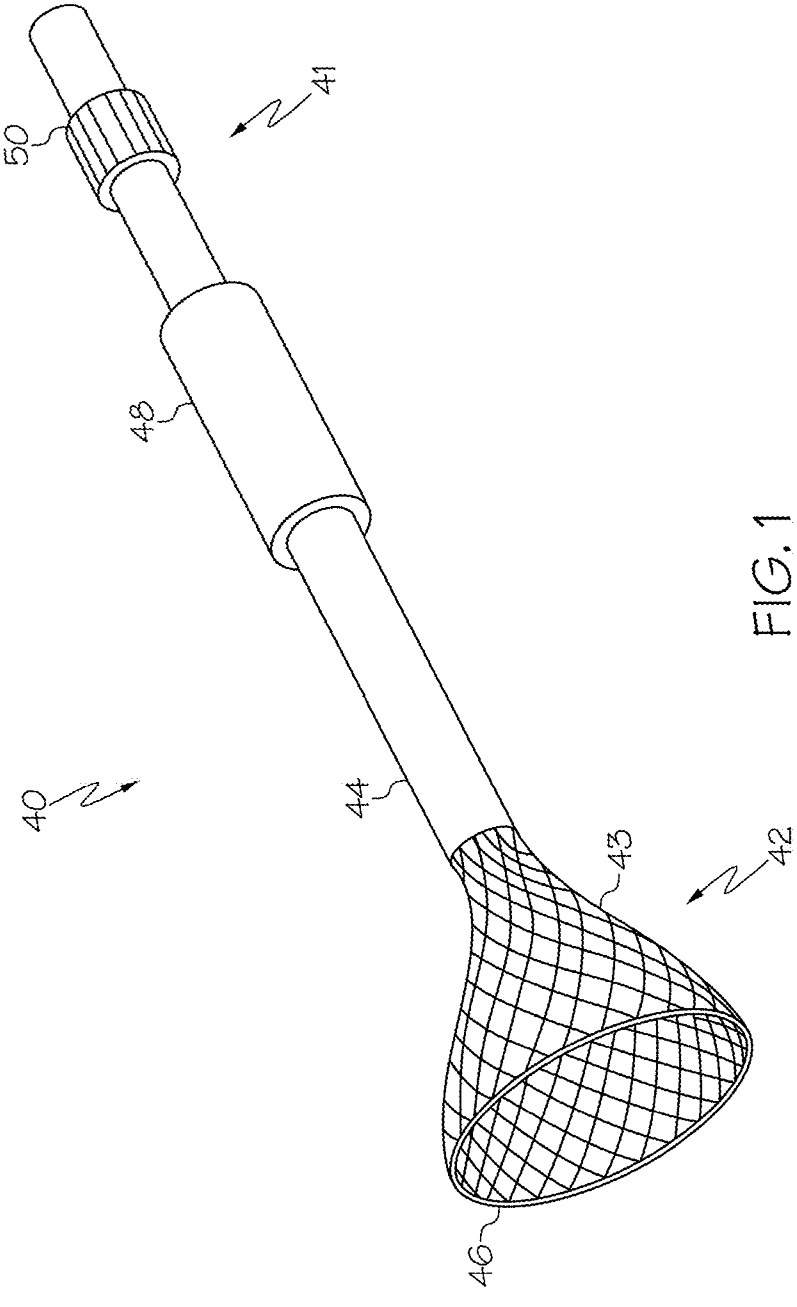
FIG. 1 illustrates a preferred embodiment of an aspiration catheter having a modified cup-shaped tip, according to the invention.
Figure 2:
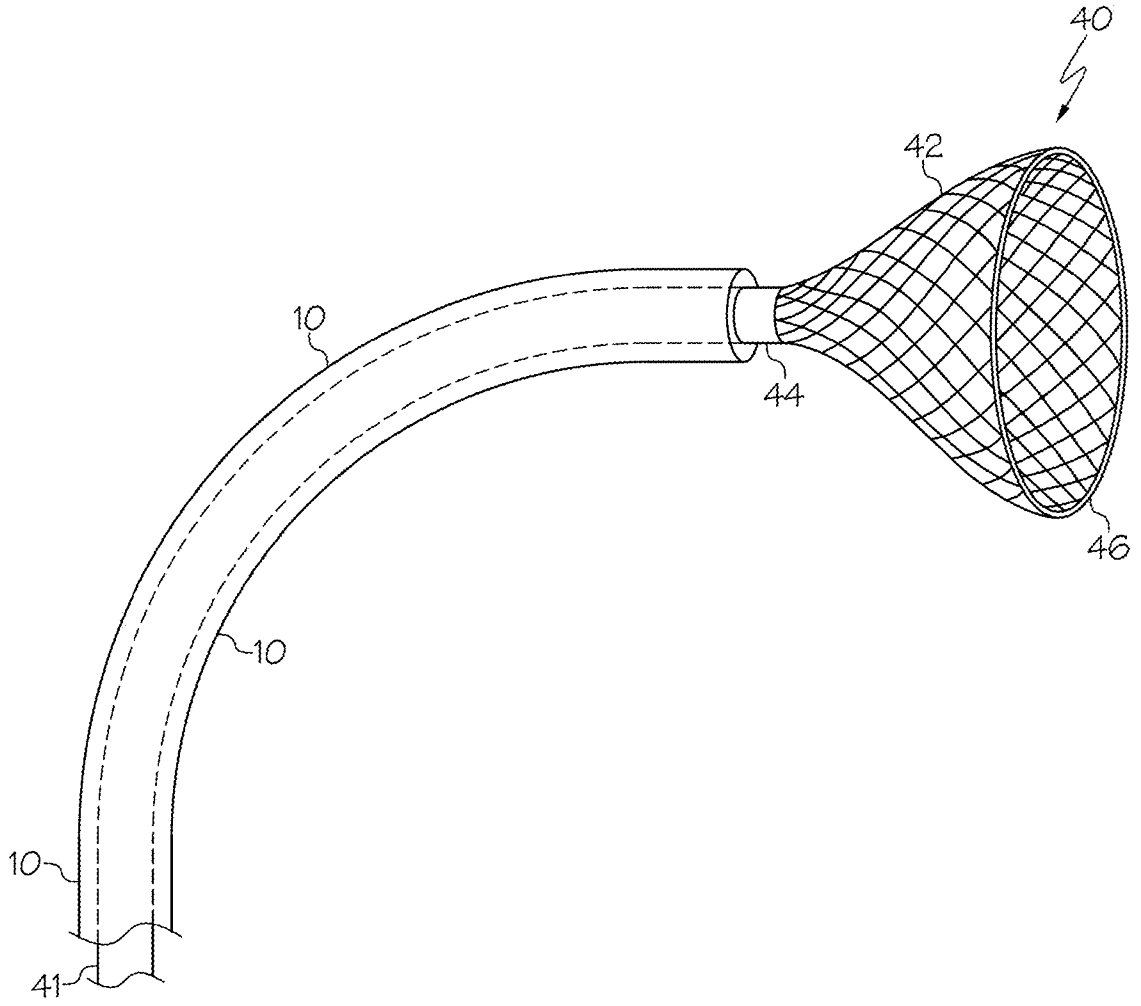
FIG. 2 illustrates the aspiration catheter of FIG. 1, with the proximal portion located within a delivery sheath.

The present invention provides a device and method for inverting the left atrial appendage (LAA). Referring to FIGS. 1 and 2, the device is a modified aspiration catheter

40 which includes a proximal end portion 41 and a distal end portion 42. The proximal portion 41 of the aspiration catheter is preferably in the form of a long, thin shaft 44 that transitions to the distal end, which is preferably in the form of an expandable/collapsable cup 42. The cup portion 42 preferably terminates at a distal edge 46, defining an outer perimeter or rim of the cup. Moving proximally from the distal edge 46, the cup 42 can include a transition section 43 that tapers from the distal edge 46 towards the proximal shaft 44 of the aspiration catheter 40. The proximal and distal portions 41, 42 of the catheter share a common internal aperture or lumen which can transmit externally applied negative pressure or suction therethrough. The transition section 43 thus promotes smooth airflow and structural stability between the rim 46 of the suction cup 42 and the proximal shaft 44.

The shaft 44 of the proximal end 41 of the catheter 40 is preferably in the form of a flexible, reinforced tube, and can include inner/outer liners and embedded coils/braids for variable stiffness and trackability, as is known in the art of aspiration catheters. The shaft 44 can also include a luer lock-type connection hub 50 at the very proximal end for connecting an external source of negative pressure (not shown) to the proximal end portion 41. The source of negative pressure can be any aspiration system or pressure/vacuum source that can supply a negative pressure through the aspiration catheter 40, as is known in the art. The luer lock connection hub 50 can provide a secure interface with the pressure/vacuum source, and can be in the form of a threaded or slip-fit connector, tested to ensure a leak-free connection.

The cup portion 42 is typically elastic, soft, rounded, and mesh-based, and intended to create "suction contact" with the interior LAA walls while minimizing trauma to the cardiac tissue. It is advantageous that the distal end 42 is preferably in the shape of a vacuum cup or suction cup, so that it can employ a pressure differential to create a seal and grip on the interior LAA walls/surface. By evacuating air from within the expanded cup 42 while in contact with the LAA interior surface, for example, as illustrated in FIGS. 4B and 4C, a lower pressure is generated inside the cup than outside, creating a vacuum which holds the cup in place, "stuck" to the interior LAA wall.

The term "suction contact" as used herein refers to the physical contact and the resulting adhesion described above between the suction cup distal end of the inventive aspiration catheter and the interior wall/surface of the LAA. The rim can help to form a seal, and with the assistance of negative pressure drawing air out from under the cup, the pressure on the outside pushes the cup against the LAA surface, creating a holding force, herein referred to as "suction contact" with the cardiac tissue. Indeed, the distal edge or outer rim of the suction cup plays a crucial role in its adhesive function because it creates a seal with the LAA surface, preventing air from entering the space between the cup and the surface. This seal, with the assistance of negative pressure, helps to create the desired suction contact, and holds the suction cup in place.

Figure 3:
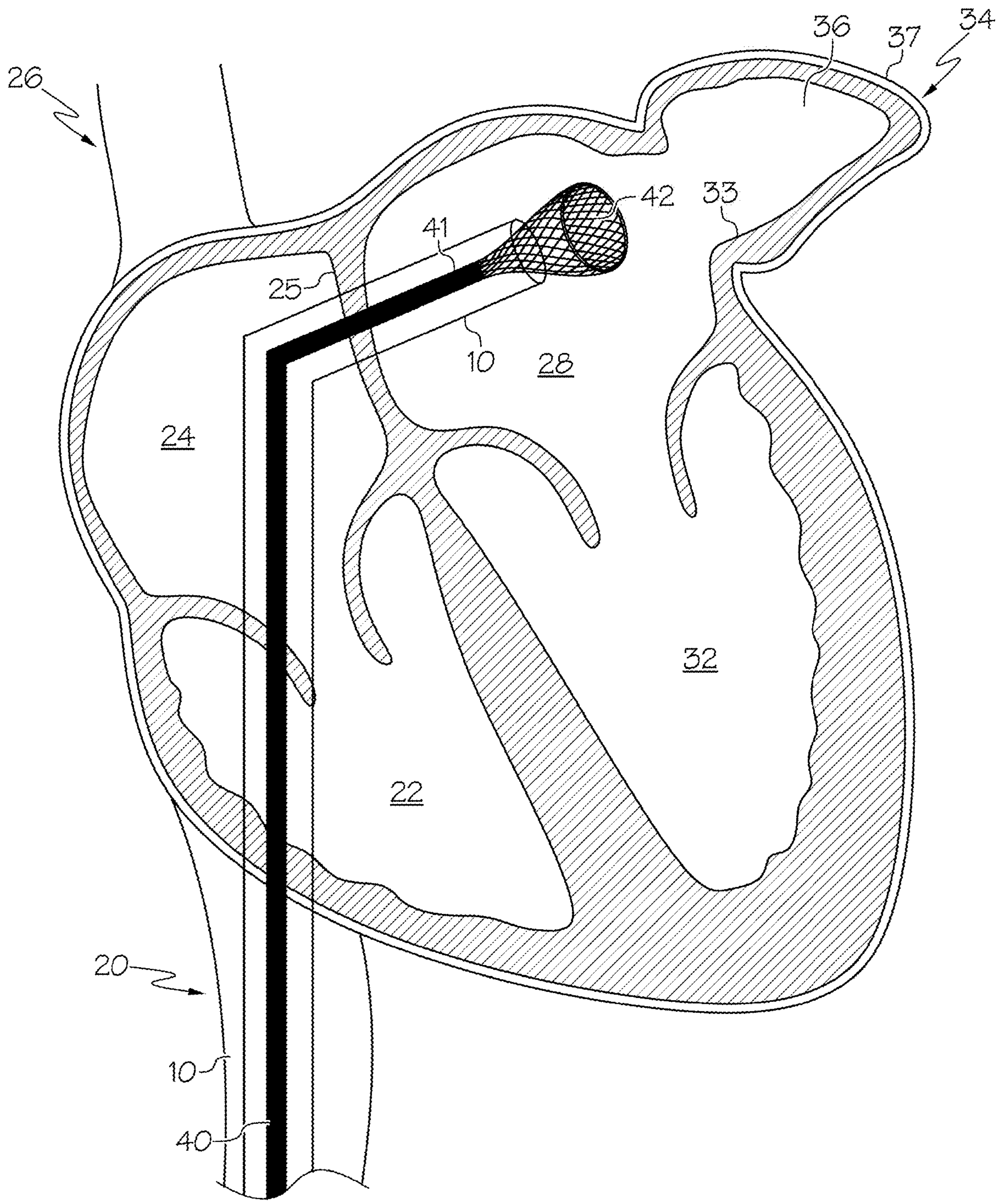
FIG. 3 illustrates location of the inventive catheter within the heart, with the cup-shaped tip located at the ostium of the LAA.

As illustrated in FIGS. 2 and 3, during maneuvering through the patient's vasculature and placement of the catheter tip near the ostium 33 of the LAA, the aspiration catheter 40 including the distal cup 42 is initially intended to slidably fit in a collapsed state within the internal diameter of an introducer/delivery sheath, such as delivery sheath 10. To accomplish this, the diameter of the aspiration catheter 40 can be about 11-12 French, and the delivery sheath 10 can be about 14 French (one French unit corresponds to 0.33 mm, or about 0.01 inches). To this end, both the proximal portion 41 and the distal portion 42 of the aspiration catheter 40 typically have an outer diameter of about 11-12 French, and share a common internal aperture or lumen having an inner diameter of 9-10 French which can transmit externally applied negative pressure or suction therethrough.

Looking at FIG. 3, the right side of the heart (which is on the left, viewing the figure) receives blood from the inferior vena cava 20 and the superior vena cava 26 into the right atrium 24, which empties into the right ventricle 22. The inferior vena cava is a large vein that carries deoxygenated blood from the lower and middle body into the right atrium 24, and the superior vena cava 26 carries deoxygenated blood from the head, neck, and upper extremities (arms and hands) into the right atrium 24. The interatrial septum 25 is a wall of tissue that lies between the right atrium 24 and the left atrium 28, and the left atrial appendage (LAA) 34 is a small pouch extending off the side of the left atrium 28.

During the procedure of inverting the LAA described herein, access to the left atrium 28 can be accomplished using a standard percutaneous technique, as is well known in the art. For example, a trans-septal access procedure into the left atrium 28 can be performed with the help of fluoroscopy and transesophageal echocardiography (TEE), in which the interatrial septum 25 is crossed using a standard transseptal access system. More specifically, peripheral venous access can be initially obtained through the femoral vein (not shown) via a transseptal puncture, which is typically performed using a transseptal sheath and needle (e.g., Brockenbrough needle) under fluoroscopic and TEE guidance. This allows access of to the right atrium 24. The initial transseptal sheath can then be exchanged for the delivery sheath 10, which can be carefully advanced over a guidewire (not shown) from the inferior vena cava 20 to the right atrium 24, and then across to the left atrium 28 via the interatrial septum 25. The delivery sheath 10 can then be steered toward the ostium 33 of the LAA 34 under TEE and fluoroscopy.

As is known in the art, a pigtail catheter (not shown) may be inserted through the delivery sheath and used to inject contrast to visualize the LAA anatomy. Multiple projections may be used to assess depth, ostium width, and lobes of the LAA. Next, the inventive aspiration catheter 40 (typically 12-French) is slidably inserted into the lumen of the delivery sheath 10 and advanced through the delivery sheath 10 into the left atrium 28, ultimately being positioned before the LAA ostium 33. The length of the aspiration catheter 40 is typically slightly greater than that of the delivery sheath (e.g., about 95 cm to 110 cm; delivery sheath: 90 cm) to ensure that the distal end of the aspiration catheter 42 can extend beyond the distal end of the delivery sheath 10, enabling compatibility and precise navigation.

The suction cup distal end 42 of the aspiration catheter is self-expanding, yet in order to fit within the delivery sheath 10 during maneuvering through the patient's vasculature and heart structures, it is intended to be maintained in a collapsed state, or at least a partially collapsed state. Looking again at FIG. 1, in order to aid in compressing the suction cup distal end 42 within the delivery sheath prior to use, the catheter 40 can also include a loader 48 on the shaft 44, between the suction cup at the distal end 42 and the luer lock 50 at the proximal end 41. The loader 48 can be used to compress the expandable components (i.e. the cup portion 42) of the aspiration catheter 40 during loading, and is preferably in the form of a smooth, cylindrical sleeve which can be positioned around and slidably moved along the length of the proximal shaft 44 to facilitate smooth entry of the collapsed cup 42 into the delivery sheath 10. The loader 48 is typically equivalent in length (i.e., about 20 mm) to the collapsed distal suction cup 42.

Figure 4A:
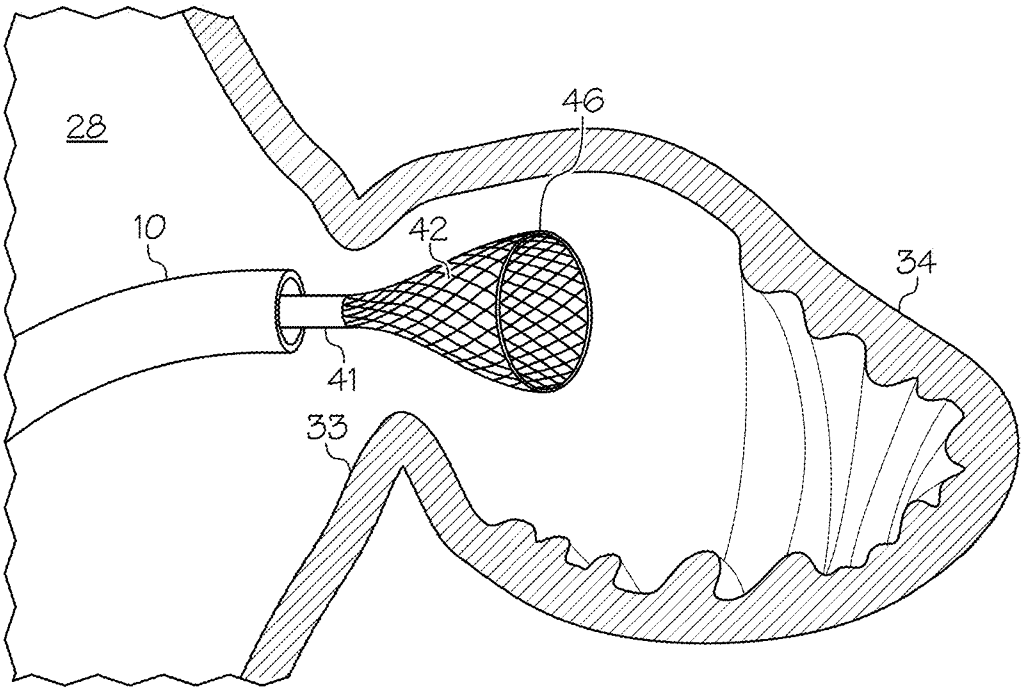
FIGS. 4A-4C illustrate sequential navigation and expansion of the inventive catheter within the heart during LAA inversion, along with the converted LAA.
Figure 4B:
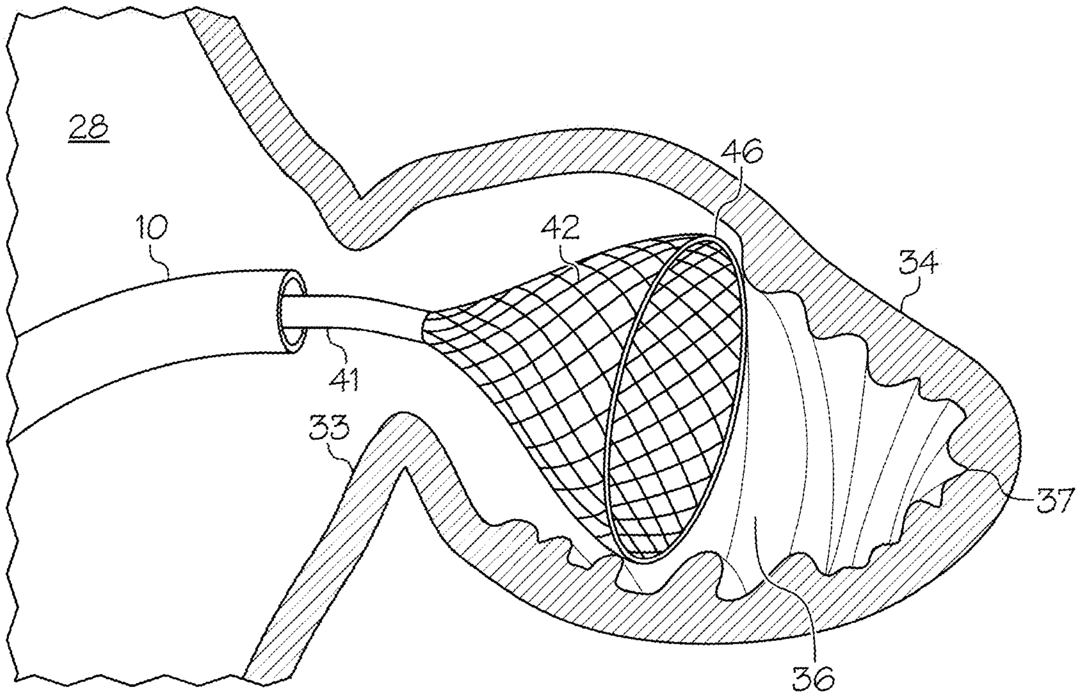
Figure 4C:
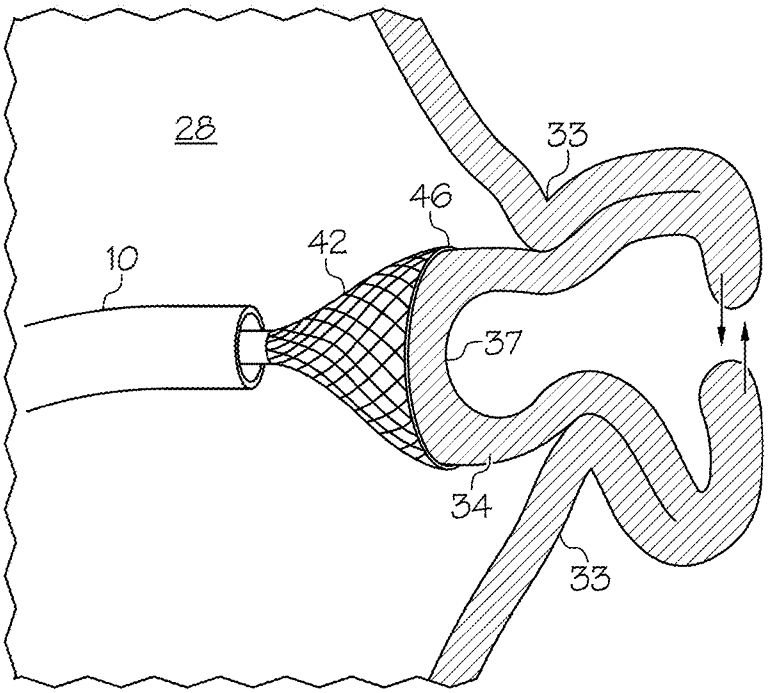
Figure 5:
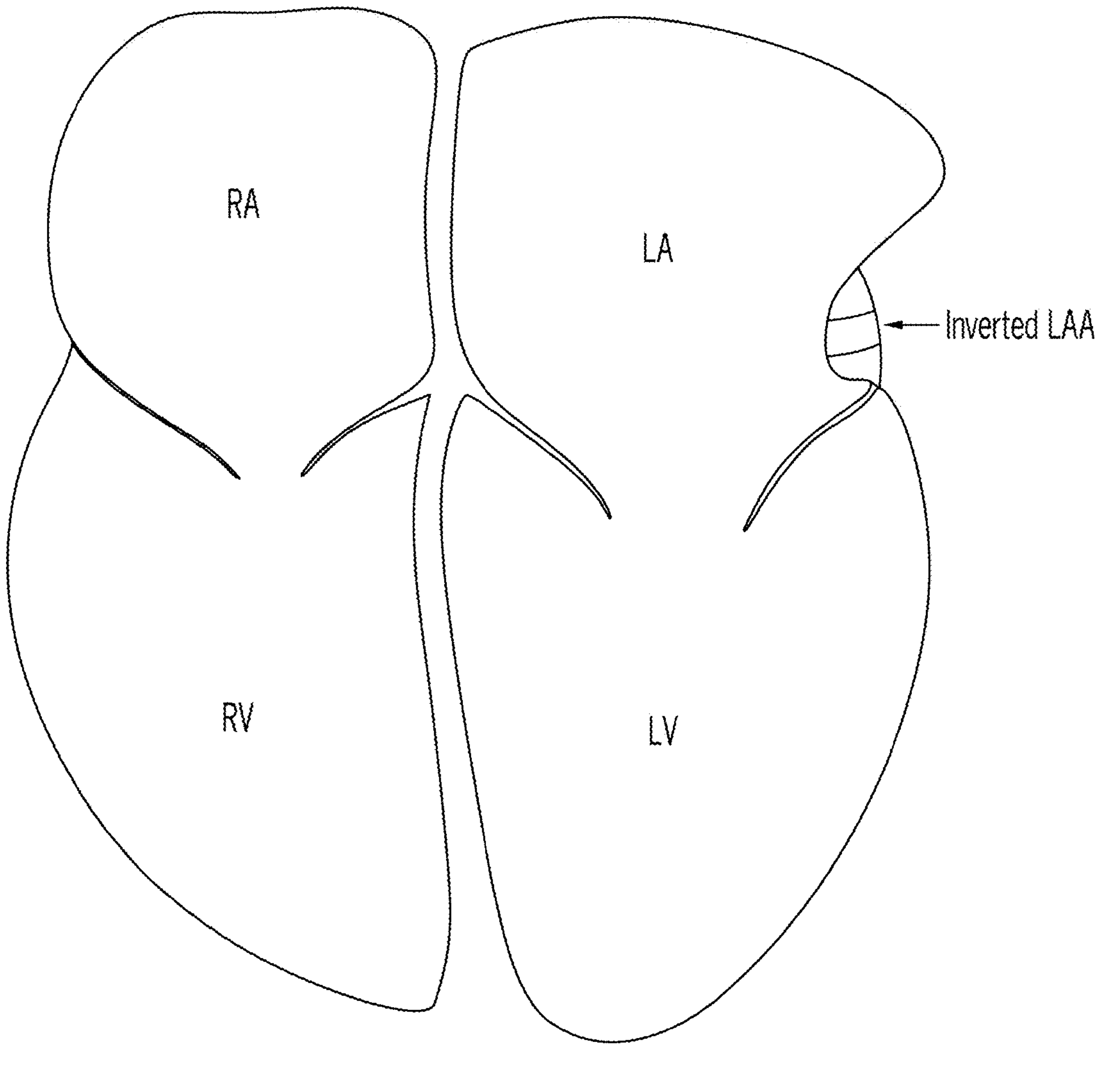
FIG. 5 is a perspective view of the heart following LAA inversion by the inventive embodiments described herein.

Once the catheter 40 has been loaded into the delivery sheath 10 and maneuvered into position before the LAA ostium 33, as illustrated in FIG. 3, the distal cup portion 42 can then be protruded from the delivery sheath and allowed to fully self-expand inside the LAA, as illustrated in FIGS. 4A and 4B. Nevertheless, the cup is also re-collapsible for reestablishment within the delivery sheath 10, for removal from the body after the procedure is finished. It is notable that the partially collapsed state of the distal cup 42, as shown in FIG. 3 and FIG. 4A, offers a safer and more atraumatic profile for navigating through the patient's vasculature, heart structures and coming to rest at the LAA ostium, as compared to the fully collapsed state inside the delivery sheath. This is because, if left to themselves, the sharp edges of the delivery sheath 10 may often damage the vasculature and heart tissues. Therefore, as illustrated in FIG. 3, the distal cup portion 42 is typically allowed to at least partially expand from the end of the delivery sheath 10 during such maneuvering and navigation.

Once in position at the LAA ostium in accordance with the clinician's determination, the suction cup distal end 42 can be fully protruded or extended from the delivery sheath 10, as illustrated in FIG. 4B. Assuming a substantially conical or hemispherical geometry upon deployment, protrusion of the catheter 40 from the distal end of the delivery sheath 10 allows the distal suction cup 42 to either be partially or fully expanded within the LAA pouch 36, which allows for making proper suction contact with the interior wall of the LAA. The cup shape of the distal end 42 is designed specifically to enhance suction contact and compression of the aspirated LAA tissue, while maintaining an atraumatic interface.

The left atrial appendage (LAA) 34 of the human heart typically begins at a mouth or ostium 33, which transitions to a body portion 36, and ultimately ends in an apex 37. To accomplish inversion of the LAA according to the present invention, the suction cup distal end 42 of the aspiration catheter 40 should initially be maneuvered within the delivery sheath 10 in a collapsed state (or partially collapsed for safety, see above), and then past the ostium 33 of the LAA and into the pouch-shaped body 36. This is typically performed by a trained clinician, preferably a cardiothoracic surgeon or interventional cardiologist, aided by transesophageal echocardiography (TEE) and fluoroscopic guidance.

The size and diameter of the LAA ostium 33 can vary significantly among patients, and can range from about 15 mm to about 32 mm, with a radius of about 7.5 mm to about 16 mm, but individual measurements can fall outside this range, depending on specific heart anatomy and pathological changes present in the patient's heart. Accurate pre-operative measurement of the patient's LAA ostium can be measured using three-dimensional TEE or computed tomography (CT), and can be crucial for selecting the appropriate size for the distal cup 42. To ensure that the distal cup end 42 of the aspiration catheter can pass through the LAA ostium 33, the outer rim of the cup, defined by the cup's distal edge 46, is typically chosen to be equal to or less than the corresponding inner diameter of the ostium 33, which as noted above is typically between about 15 mm to about 32 mm, but can vary from patient to patient.

The length of the cup-shaped distal portion 42 can be about 20 mm, but can range between about 15 mm to about 30 mm, depending on patient anatomy. The degree of self-expansion of the cup 42 within the LAA pouch can be determined by the clinician, based on the specific size and shape of the LAA being inverted. More specifically, after being navigated past the ostium 33 of the LAA, at least the distal edge 46 of the cup can be protruded outside of the delivery sheath 10 so that the cup 42 can partially, and then fully if needed, self-expand and make contact with the interior wall of the LAA. Upon the addition of appropriate suction through the aperture of the proximal portion 41, the resulting suction contact made between the cup 42 and the inner surface or interior wall of the LAA can facilitate inversion.

Inversion of the LAA is achieved by creating a vacuum within the cup, and allowing the clinician to pull the LAA through the LAA ostium. The "best" shape for any suction cup depends on the particular application and the surface it needs to adhere to. Curved type suction cups are typically better for uneven, textured, or curved surfaces such as the LAA, while flat cups are ideal for smooth, flat, or slightly curved surfaces. Oval cups are suitable for narrow or elongated objects, and bell-shaped cups can handle both convex and concave surfaces. While the distal cup portion 42 can be in the form of any of the types of cups described above, as needed for a particular patient, preferably the cup is a curved suction cup as illustrated herein, having a substantially circular distal edge 46 which is optimal for use on the uneven and curved surfaces of the interior LAA.

Looking at FIGS. 3 and 4A-4C, during the inversion procedure, the distal edge 46 of the suction cup portion of the aspiration catheter can be passed through the LAA ostium 33 and then deployed from the delivery sheath 10. At this point, noting the expansion of the cup between FIGS. 4A and 4B, partial expansion up to the full length expansion of the cup 42 can be facilitated within the LAA 34 and used in combination with activation of the vacuum source to make suction contact with the LAA and pull it inside out through the ostium 33, as shown in FIG. 4C. Once the clinician connects the pressure/vacuum source (such as a computer-assisted vacuum system, a motorized external suction device, or a large syringe) to the proximal portion of the aspiration catheter 40, and negative pressure is transmitted to the expanded cup-shaped distal portion 42, the suction contact can cause the cup to attach to and pull the inner walls of the LAA. The clinician can then withdraw the aspiration catheter 40 inward, typically in a direction towards the interatrial septum 25, so that the LAA portion making suction contact with the cup-shaped distal portion 42 can be pulled through the ostium 33, leading to inversion of the LAA pouch. As a non-limiting example, in a particular patient the LAA apex 37, along with a portion of the side walls 36, may be the desired areas for making suction contact with the expanded distal cup 42 of the aspiration catheter 40, for pulling through the ostium 33.

During the inversion procedure the clinician can recapture and reposition the expanded distal cup 42 onto the interior surface of the LAA multiple times, as needed, prior to final deployment and withdrawal of the LAA, allowing for accurate placement of suction and successful LAA inversion. Once positioning is satisfactory, the captured interior wall of the LAA 34 can then be pulled or otherwise displaced through the ostium 33 via the suction contact between the cup 42 and the interior LAA wall. Once inverted, such that blockage of the LAA ostium 33 by the inverted body of the LAA is accomplished, the vacuum source can be deactivated or otherwise removed/turned off so that suction contact is broken, causing the distal cup 42 to detach from the LAA. In this manner, the LAA can be caused to assume an "inverted hat" configuration, as illustrated in FIG. 4C. This inverted hat configuration is stable; there is no need to use further closure devices. Successful LAA inversion performed in the manner described above can achieve blockage of any future blood entry into the LAA, by virtue of the inverted LAA muscular wall blocking the ostium. No clips, stents, springs, glues or other closure devices need to be left behind following the procedure.

The inversion procedure avoids any puncture or chemical injection, and involves only the temporary deployment of negative pressure through a soft, cup-shaped suction catheter. In this context, no cutting, stitching, clipping, or glue is required to maintain the inverted state, making the technique inherently safer and less invasive than conventional procedures.

Vacuum pressures used for the inventive inversion method can have an acceptable range of about −50 to −600 mmHg (approx. −6.7 to −80 kPa), and a preferred operating range of about −100 to −200 mmHg initially, which can be adjusted under TEE/fluoroscopy. It is recommended to begin with moderate suction (e.g., −100 to −200 mmHg) and then gradually increase as needed, based on TEE/fluoroscopy guidance and device response. It is also preferable to use intermittent suction pulses, rather than continuous high vacuum, for safety. There is an increased risk upon exceeding −600 mmHg, which can lead to endothelial trauma, hemolysis, LAA collapse, or air embolism. A typical 60 mL Toomey syringe can generate −300 to −600 mmHg of vacuum pressure momentarily. Wall-mounted or portable aspiration pumps can provide an adjustable vacuum, which is often set between −100 and −400 mmHg for LAA procedures. The system should include vacuum regulators to prevent excessive negative pressure that could cause tissue injury or hemolysis.

The inventive LAA inversion method described herein is preferably intended for patients with permanent (chronic) atrial fibrillation, where no effective atrial contraction is present. It is notable that left atrial pressure (LAP) is generally too low to push out the inverted LAA, such that there is little risk that the partially inverted LAA will be reversed by the continuous pressure supplied by the contracting left atrium. The average normal left atrial pressure (LAP) is 8 mm Hg, with a range of 2 mm Hg to 12 mm Hg, and in patients with long-term atrial fibrillation the left atrium does not completely contract making the LAP in these patients even lower than normal. Instead, the muscle fibers making up the atrial wall fibrillate at an irregular and high frequency (>400 bpm). Such structural and functional changes of the heart under these conditions can lead to a lack of active and sustained contraction of the left atrial muscle, i.e. a weak "atrial kick", which normally occurs during late diastole. Since the strength of contraction is so weak, the pressure generated within the left atrium is not strong enough to push or "pop" the partially inverted LAA back out.

In addition to the low risk of reversal, the risk is considered to be very low that the partially inverted LAA can become fully inverted. That is, the inverted LAA will not extend into the left atrium to an extent that it can obstruct mitral valve outflow. This is because the continuous pressure supplied by the return of blood into the left atrium is believed to be sufficient to prevent complete inversion. Moreover, the ostium is typically narrow and acts as a mechanical constraint, compressing the inverted LAA within. This compression effectively limits the depth of inversion of the LAA into the left atrium, thereby further reducing the risk of excessive protrusion of the inverted LAA and potential interference with mitral valve function. Over time, the body's natural healing processes will cover the inverted LAA with granulating endothelial tissue, effectively sealing it off by creating fibrotic deposits over and around it.

In light of the above discussion, it is believed that the "inverted hat" shape of the inverted LAA is stable, and can resist being inverted further in or being pushed back out without the need for sewing, clipping, or other form of constraint. The phrase "inverted hat" in the medical lexicon is previously and better known as a radiologic sign, for example, as can be seen on a frontal pelvic radiograph, in which the "brim" of the hat is formed by the transverse processes of an intervertebral disc, and the inverted "dome" is formed by the vertebral disc body, beneath. Analogously, according to the present invention, the "dome" of the (upside down) hat is formed by the portion of the interior LAA wall (e.g., the apex 37) that has been physically pulled through the ostium, and the "brim" of the hat is formed by the ostium 33 and the adjacent interior walls of the LAA.

Most clinical aspiration catheters are constructed from a combination of materials designed for flexibility, structural support, and smooth navigation within the body. Common materials for use with the present invention can include nitinol, PTFE (teflon), stainless steel, and polymer blends. Nitinol is a unique nickel-titanium alloy known as a "smart material" for its extraordinary shape memory and superelasticity, allowing it to return to a pre-deformed shape or exhibit extreme flexibility and resistance to kinking, making it crucial in medical devices such as stents, surgical tools, and eyeglass frames. PTFE is commonly used for inner liners, offering low friction and ease of aspiration. Stainless steel provides structural integrity and kink resistance, often used in braiding, and polymer blends are often used in outer jackets, varying in stiffness to provide different levels of support and flexibility. Other flexible support segments may also be used, and are typically made of materials like nylon, to provide support and stability in specific areas of the catheter.

As noted above, the cup-shaped tip 42 of the aspiration catheter is compressed within the 14-French delivery sheath 10 and advanced inside it once the distal tip of delivery sheath is positioned in the left atrium, directly opposite the ostium of the LAA, and it is extruded from the delivery sheath and expanded after location within the LAA. To allow such reversible compression and expansion, the cup structure is preferably made of Nitinol, or a similar superelastic material, having braided construction in the form of a mesh-like structure which enables the cup shape to self-expand from its compressed state and adapt to the complex anatomy of the inner LAA. This unique self-expanding property, along with its shape memory ability, makes nitinol ideal for use as the cup portion of the aspiration catheter.

In contrast to the cup-shaped distal end 42, the material of the proximal end 41 of the aspiration catheter 40 is typically made from biocompatible, flexible materials like polyurethane or silicone. Both the proximal tube portion 41 and the distal cup portion 42 of the aspiration catheter are intended to be flexible, soft and atraumatic to navigate through the heart structures without causing damage to the vasculature or the cardiac tissue. The distal edge 46 of the cup can be radiopaque marked to enhance visibility under fluoroscopy, allowing for precise positioning within the LAA. A hydrophilic coating can also be included on the catheter to reduce friction during insertion and navigation, as is known in the art. Lubricious coatings can further enhance ease of navigation and reduce friction. Antithrombogenic materials, such as heparin or hirudin, can also be employed to prevent blood clots within the catheter.

Upon continued development of the present invention, it was determined that further development of the distal cup portion of the aspiration catheter was needed, because the inventor was concerned with the problem of pulling the left atrial appendage too far through the ostium. Specifically, it was discovered that simply turning off the external suction source at the proximal end following inversion of the LAA is an uncontrolled and thus unreliable means for releasing the suction cup from the inverted LAA. For example, if "suction contact" between the distal suction cup and the LAA is broken or otherwise released too late, the LAA can be inadvertently pulled too far into the left atrium, such that the "inverted hat" can become a completely "inside out hat". Should this occur, the inside out LAA may interfere with or even block the flow of blood entering the left atrium. In addition, if "suction contact" is broken too early, then an incomplete and unstable inverted hat configuration may result, which can allow the partially inverted LAA to slip or "pop" back out of the ostium after suction is removed. As such, an innovation is provided herein for a means to collapse the distal suction cup around the inverted LAA in order to stabilize the inverted LAA in the "inverted hat" configuration, followed by a controlled release of the suction cup from the stable, inverted LAA.

As noted above, "suction contact" occurs when the distal edge or outer rim of the suction cup creates a seal with the LAA surface. This seal, with the assistance of negative pressure from the external suction source, helps to create the desired "suction contact", and holds the suction cup in place on the inside surface of the LAA. The novel torsional suction cup described below and illustrated in FIGS. 6-8 provides a means for the clinician to efficiently control the release of the suction cup from the inverted LAA. This embodiment is specifically useful for stabilizing the inverted hat configuration prior to such controlled release, thereby improving the chances for successful LAA inversion without the need to implant or leave behind any external sutures, clips, ties, or other objects.

Figure 6A:
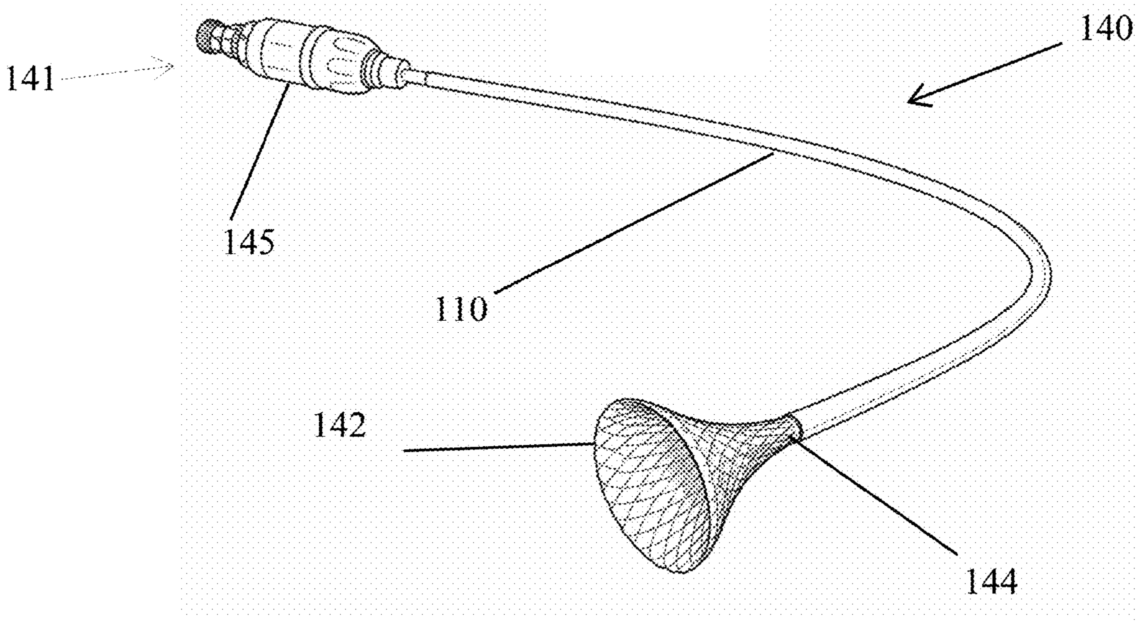
FIGS. 6A and 6B illustrate a preferred embodiment according to the present invention of an aspiration catheter having a torsional, self-expanding distal cup.
Figure 6B:
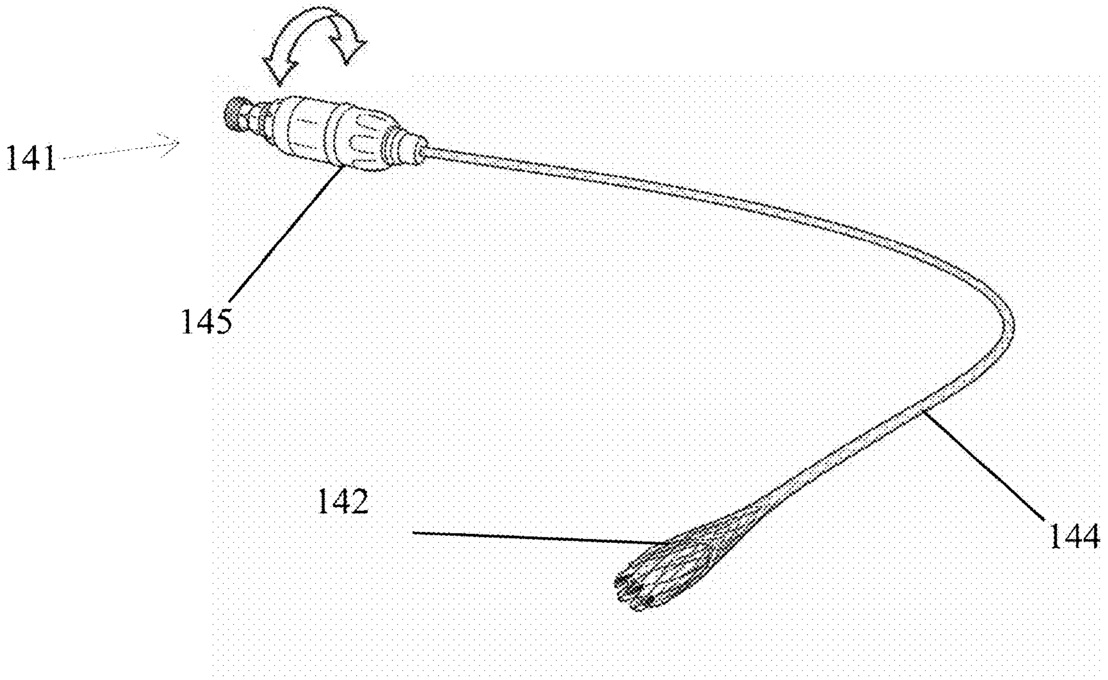

A preferred embodiment of an extendable, torqueable, self-expanding suction cup 142 according to the invention is shown in FIGS. 6A, 6B, 7A, 7B, 8A, 8B, and 8C, and described in detail below. A combined medical device in the form of a torsional aspiration catheter 140 is illustrated in FIGS. 6A and 6B. Looking at FIG. 6A, the inventive torsional catheter 140 includes an actively torque-driven mechanism, referred to herein as a "twist-to-compress" distal suction cup 142, a torque handle 145 located at the proximal end 141, and a catheter sheath 110 encasing a "torqueable" (i.e., "torque-capable") catheter shaft 144. A torsional or rotational force, illustrated by the curved arrow in FIG. 6B about the torque handle 145, can be created proximally and transmitted along the torqueable shaft 144 and directly to the twist-to-compress distal cup 142. Thus, torque on the distal suction cup 142 can be controlled by the clinician at the catheter's proximal end 141. The catheter sheath 110, in addition to encasing the catheter shaft 144, can also encase and guide the suction cup 142 in a collapsed state to its destination outside the ostium of the LAA, as described in more detail above, prior to the cup's self-expansion out of the distal end of the sheath 110. FIG. 6A illustrates the distal cup 142 after extending past the distal end of the catheter sheath 110, allowing it to naturally self-expand.

Torsion is the main mechanism of action for the modified LAA aspiration catheter shown in FIGS. 6A and 6B. For example, the catheter 144 can be in the form of a "cable tube", as is known in the art, which is formed by helically twisted wires over a core wire, but with the core wire removed to create a lumen inside the structure. When torque is applied in the twist direction of the cable tube, the wires will move towards each other. With a sufficiently stiff base material (e.g. stainless steel), the wires' compression of each other becomes minimal, translating deformation into rotation of the shaft itself, and a high transmission of torque to the distal cup is achieved. FIG. 6B illustrates the aspiration catheter 140 of FIG. 6A without the sheath 110 covering, so that it can be appreciated that the catheter shaft 144 connects the torsional distal suction cup 142 with the proximal torque handle 145.

The suction cup 142 and the catheter shaft 144 are preferably formed from a suitable biocompatible metal. For example, both the suction cup 142 and the catheter shaft 144 can be made of a resilient material such as nitinol mesh, with the suction cup's natural shape preferably being in an expanded (self-expanding) configuration, such that the torque handle actuation device 145, via transmission of torque through the catheter shaft 144, functions to bring the expanded suction cup 142 into a collapsed or low profile configuration. Alternatively, the suction cup 142 can have a natural shape in the collapsed configuration, such that it is not self-expanding but self-collapsing, and the actuation device can function to bring the collapsed suction cup into the expanded configuration. While nitinol mesh is the preferred material for the suction cup 142 and the catheter shaft 144, they can also be made from any other sufficient malleable but non-resilient material which can allow torque applied by the actuation device 145 to transform the suction cup between the expanded and collapsed state.

As noted above, the catheter shaft 144 is connected to and preferably continuous with the distal suction cup 142 at its distal end, such that torque applied to the torqueable shaft 144 by the torque handle 145 is transmitted to the distal cup 142. An external suction source (not shown) can be attached via a connection with the torque handle 145 to the lumen of the catheter shaft 144, which shares the lumen with the suction cup 142, and vacuum/suction can be provided through the lumen to the distal suction cup 142. In a preferred embodiment, the distal suction cup 142 interfaces with the torqueable catheter shaft 144, which interfaces with a proximal actuation device such as the torque handle 145. Actuation devices for torqueable catheter shafts are known in the art, and can use mechanical (pull-wires, inner cores), hydraulic, pneumatic, or even magnetic/piezoelectric systems to control torque, often employing multi-lumen designs with pull wires or specialized cable tubes for precise torque transmission.

Torsional rotation or torque is illustrated as a curved arrow in FIG. 6B about the torque handle 145, and can be controlled by the clinician and transmitted through the catheter shaft 144 and onward to the distal cup 142, providing a precisely timed mechanical collapse of the suction cup 142. Specifically, FIG. 6B, FIG. 7B, and FIG. 8B all show the cup 142 in the collapsed state, and conversion between the expanded state shown in FIG. 6A and by manipulating the torque handle 145 the clinician can control the timing of the release of the suction cup 142 from the inverted LAA 34 (see FIGS. 8A-8C).

Figure 7A:
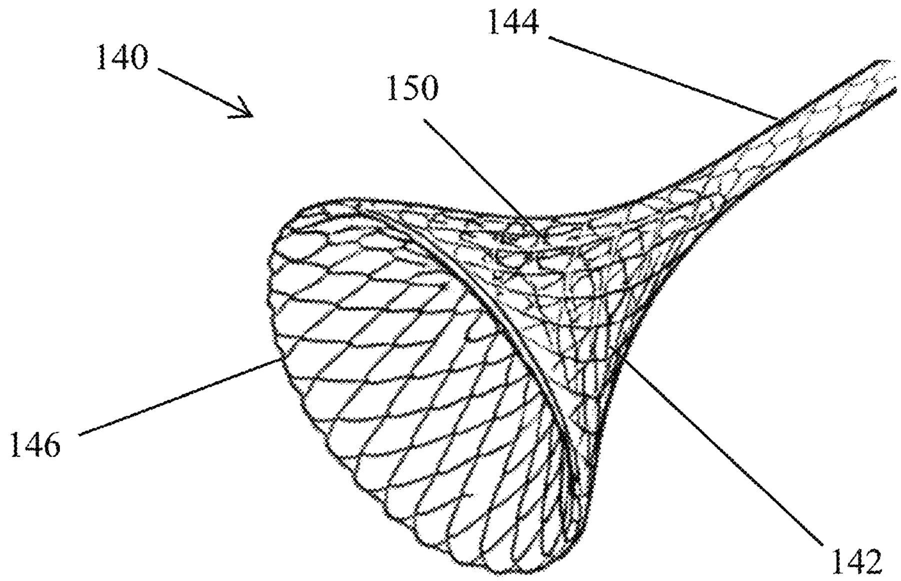
FIGS. 7A and 7B are close-up illustrations of the torsional, self-expanding distal cup of FIGS. 6A and 6B.
Figure 7B:
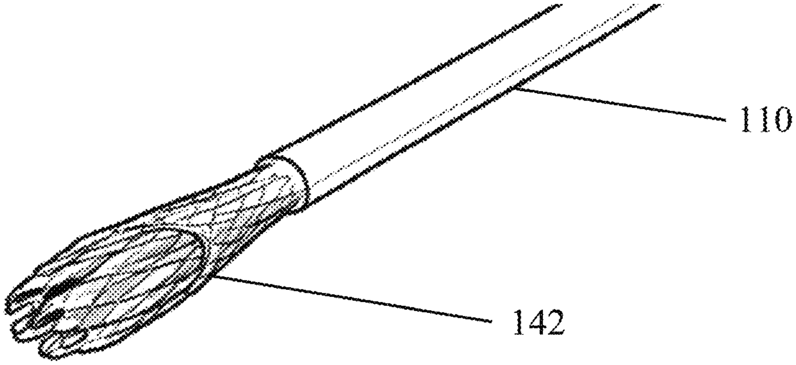

A close-up view of the torsional suction cup 142 is illustrated in FIGS. 7A and 7B. A fully expanded, distal funnel or cup 142 is shown in FIG. 7A, formed from a braided nitinol mesh structure, in the form of spiral torsion ribs or radial struts 150. The mesh architecture 150 is preferably torsion-responsive, such that rotation of the proximal torque handle 145 induces radial contraction of catheter shaft 144 and then the distal cup 142, causing a progressive reduction in the cup's diameter and length. FIG. 7A illustrates the resting posture of the cup 142, in which no rotation is required by the clinician at the proximal end to cause the naturally self-expanding suction cup to assume this configuration. Like the earlier embodiments of the distal suction cup disclosed herein, the twist-to-compress cup 142 embodiment is adapted to transition between a collapsed state inside the catheter sheath 110 and an expanded state when it is protruded from the catheter sheath 110. When fully expanded, as shown in FIGS. 6A, 7A, and 8A, the cup 142 is in its maximum diameter configuration, and the struts 150 are relaxed and exhibit their native flared geometry.

The self-expanding suction cup 142 forms a funnel-like structure when fully expanded, as shown in FIG. 7A, and terminates at a distal edge 146 defining an outer perimeter, or rim. A transition section of the cup tapers from the rim 146 towards the torqueable catheter shaft 144. Like the embodiments illustrated earlier, the catheter shaft 144 and the suction cup 142 share a common internal aperture or lumen, which can transmit externally applied suction, allowing the cup 142 to create "suction contact" with the interior LAA wall 34 while minimizing trauma to the cardiac tissue. FIG. 7B shows the distal suction cup in a fully collapsed configuration, which can be caused by the clinician providing torque at the proximal end.

In use, the proximal torque handle 145 can provide a defined rotational input which in turn is transmitted via the catheter shaft 144 to the distal cup 142. The primary goal is to achieve an approximately 1:1 ratio or 1:1 torque transmission, meaning one full turn of the proximal torque handle 145 results in full collapse of the naturally self-expanding distal cup 142 (see, e.g. FIGS. 6A, 7A, and 8A). To achieve high torsional stiffness without losing flexibility, the catheter shaft 144 preferably employs nitinol or stainless steel braids/coils. Such catheters have previously been used to navigate tortuous anatomy such as the vasculature. Thus, while such devices have previously been used to control and guide a catheter tip for procedures such as coronary angiography, electrophysiology, and urology, such torque-capable catheters have not previously been used to collapse and/or expand a distal suction cup for an LAA inversion procedure. In any event, the rotational torque created by the clinician at the proximal end induces torsional deformation and collapse of the distal cup structure, capturing the inverted LAA within the collapsed cup, and stabilizing it prior to final release (see FIGS. 8A-8C).

Figure 8A:
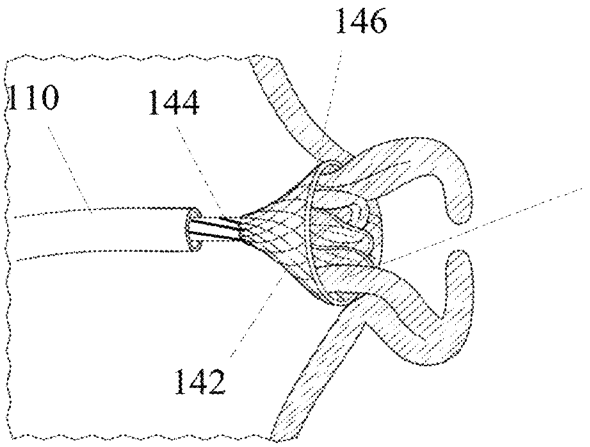
FIGS. 8A-8C sequentially illustrate the inversion, stabilization, and release of the left atrial appendage by the torsional, self-expanding distal cup of FIGS. 7A and 7B, according to the present invention.
Figure 8C:
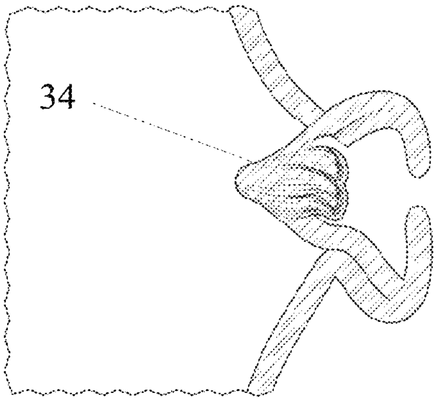
Figure 8B:
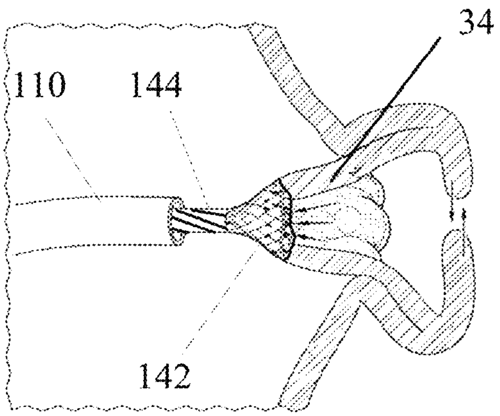

The stabilization and release of the inverted LAA in the inverted hat configuration is sequentially illustrated in FIGS. 8A-8C. Specifically, FIG. 8A illustrates the expanded suction cup 142 with its rim 146 fully extended around the captured LAA body 34, the cup having successfully pulled the inverted LAA 34 into the "inverted hat" configuration described above. FIG. 8B illustrates the distal suction cup 142 in a manually collapsed state with the inverted LAA 34 being compressed within the cup. As noted above, collapse of the suction cup 142 is controlled by the clinician by using a torque handle 145 at the proximal end of the catheter (see FIG. 6A). By collapsing the suction cup 142 as shown in FIG. 8B, the clinician has the ability to compress and stabilize the inverted LAA within the collapsed cup, allowing the inverted hat configuration to find a new equilibrium, becoming established and fixed. Subsequent re-expansion of the distal cup following this compression can lead to a controlled release of the inverted LAA from the cup, typically along with, but potentially without having to turn off the external suction source. Thus, when torque is removed proximally and the cup 142 naturally self-expands once again, the compressed, inverted LAA may at least partially, if not completely, break "suction contact" with the expanding suction cup. Nevertheless, the external suction is typically turned off during or shortly following removal of torque and re-expansion of the suction cup to ensure the full release of the cup from the cardiac tissue to provide a stable, inverted LAA (34, as shown in FIG. 8C) with no external clips, ties, or other objects left behind.

As noted, when used to perform the inventive LAA inversion method, the inventive torsional suction cup 142 can advantageously compress and stabilize the inverted LAA 34 prior to release, and therefore can be more efficient and reliable compared to prior art suction cups or other known LAA inversion systems. In addition, the radial collapse of the distal cup 142 around the inverted LAA 34 can provide improved control of the timing for the release of the LAA from the cup, which may be accomplished simply by manipulating the hub's torque handle 145, thus providing more precision and control over forming a stable inverted hat configuration. As a result, after inversion, the inverted LAA tissue 34 confined within the cup 142 can be gently but firmly compressed and stabilized. Rotation of the torque handle 145 in the opposite direction will cause radial re-expansion of the cup, and, upon expansion, release the cup from the inverted LAA. The LAA is now compressed in the inverted hat configuration (see FIG. 8C), and can remain as a stable structure within the LAA ostium. Suction may be turned off shortly after, or simultaneously with the release of the torque handle and re-expansion of the suction cup, to ensure that the LAA is completely released from the cup prior to withdrawal of the aspiration catheter from the patient.

As noted above, the torqueable catheter shaft or body can be made using materials like braided stainless steel or nitinol reinforcement to efficiently transmit a twisting force (torque) from the proximal handle to the distal end with minimal loss (ideally a 1:1 torque response). This allows the clinician to control the orientation of the distal cup precisely. The proximal torque handle serves as a control mechanism at the clinician's end of the catheter (the handle) and allows for the application of a controlled torsional or rotational force, which translates into a shape-changing action at the distal cup. This system offers enhanced control and maneuverability in minimally invasive procedures by converting a simple rotational input into a targeted, complex mechanical action at the treatment site.

Preclinical experimental studies are still needed to investigate the value of the inventive LAA inversion device and method described herein; for example, by comparing its feasibility, safety, and effectiveness to traditional oral anticoagulation therapy, as well as to other, more established atrial occlusion devices, such as the Watchman™ or AtriClip™ devices. Nevertheless, the present invention is intended to be used to invert the LAA and to prevent future thrombus formation in patients suffering from atrial fibrillation (AFib) in whom long-term anticoagulants are contraindicated. The inventive device and method can subsequently reduce the risk of embolic stroke without the need for implantation of clips, stents, or other closure devices into the heart.

While the present invention has been illustrated by the description of embodiments and examples thereof, it is not intended to restrict or in any way limit the scope of the appended claims to such details. Additional advantages and modifications will be readily apparent to those skilled in the art. Accordingly, departures may be made from such details without departing from the scope of the invention.

What is claimed is:

1. A catheter device for inverting a left atrial appendage, the device comprising:
- a) a distal self-expanding, radially torsional, twist-to-compress suction cup; and
- b) a proximal torqueable aspiration catheter shaft, the proximal torqueable aspiration catheter shaft including:
  - i) a proximal end attached to a torque handle; and
  - ii) a distal end connected to the distal self-expanding, radially torsional, twist-to-compress suction cup for transmitting torque applied by the torque handle, wherein the distal self-expanding, radially torsional, twist-to-compress suction cup is torsion-responsive to rotation of the torque handle to cause radial contraction and a progressive reduction in a diameter and length of the distal self-expanding, radially torsional, twist-to-compress suction cup, and wherein removal of the torsion created at the torque handle allows the suction cup to radially re-expand.

2. The device of claim 1, wherein the distal self-expanding, radially torsional, twist-to-compress suction cup comprises a braided nitinol mesh structure having radial struts that connect to the distal end of the proximal torqueable aspiration catheter shaft, and wherein the distal self-expanding, radially torsional, twist-to-compress suction cup is responsive to torque applied by rotation of the torque handle.

3. The device of claim 1, wherein the torque handle is operably connected to an external suction source, wherein the proximal torqueable aspiration catheter shaft includes a lumen therethrough which is operably connected to the torque handle such that the lumen of the proximal torqueable aspiration catheter shaft is in fluid communication with the external suction source, and wherein the distal self-expanding, radially torsional, twist-to-compress suction cup includes a second lumen operably connected to the lumen of the proximal torqueable aspiration catheter shaft such that the second lumen is also in fluid communication with the external suction source.

4. The device of claim 3, wherein the distal self-expanding, radially torsional, twist-to-compress suction cup is operable to make suction contact with a left atrial appendage (LAA) of a patient's heart and to compress and stabilize the LAA in an inverted hat configuration in response to torsion created at the torque handle, and wherein the subsequent removal of torsion and release of suction contact with the inverted LAA causes the LAA to remain in the inverted hat configuration without the need to implant a closure device.

5. The device of claim 4, wherein the distal self-expanding, radially torsional, twist-to-compress suction cup terminates at a distal edge defining an outer rim configured for creating a seal with an interior wall of the LAA, and wherein the outer rim can be configured to be repositioned and recaptured onto the interior LAA wall to cause inversion upon pulling the LAA through the LAA ostium.

6. An aspiration catheter for inverting a left atrial appendage (LAA), the aspiration catheter comprising:
- i) a proximal portion for attachment to a negative pressure source, the proximal portion including a torque handle at the proximal end and a torqueable catheter shaft connected to the torque handle; and
- ii) a distal portion consisting of a self-expanding, radially torsional suction cup comprising a braided nitinol mesh structure in the form of radial struts that are torsion-responsive to rotation of the torque handle to cause radial contraction and a progressive reduction in a diameter and length of the self-expanding, radially torsional suction cup, wherein the proximal and distal portions share a common internal lumen for transmitting externally applied negative pressure therethrough, wherein the self-expanding, radially torsional suction cup is adapted for pulling the LAA through the LAA ostium into an inverted hat configuration, wherein the self-expanding, radially torsional suction cup is caused to radially collapse around, compress, and stabilize the LAA in the inverted hat configuration in response to torsion created at the torque handle, wherein removal of the torsion created at the torque handle allows the self-expanding, radially torsional suction cup to radially re-expand and become configured to controllably release suction contact from the inverted LAA so that the LAA remains in the inverted hat configuration without the need to implant a closure device.

7. The aspiration catheter of claim 6, wherein the self-expanding, radially torsional suction cup terminates at a distal edge defining an outer rim configured for creating a seal with an interior wall of the LAA, and wherein the outer rim can be configured to be repositioned and recaptured onto the interior LAA wall to assure inversion upon pulling the LAA through the LAA ostium.

8. A method for inverting the left atrial appendage (LAA) of a patient's heart, the method comprising the steps of:
- a) providing an aspiration catheter for maneuvering through a patient's vasculature and into the left atrium, the aspiration catheter comprising: (i) a proximal portion for attachment to a negative pressure source, the proximal portion comprising a torque handle and a torqueable aspiration catheter shaft; and (ii) a distal portion comprising a self-expanding, radially torsional suction cup connectable to the torqueable aspiration catheter shaft for making suction contact with an interior wall of the LAA, wherein the self-expanding, radially torsional suction cup is responsive to rotation of the torque handle to cause radial contraction and a progressive reduction in a diameter and length of the self-expanding, radially torsional suction cup, and wherein removing the torsion applied at the torque handle allows the self-expanding, radially torsional suction cup to radially re-expand;
- b) maneuvering the torqueable aspiration catheter shaft through a patient's vasculature and heart and into the left atrium of the heart;
- c) maneuvering the self-expanding, radially torsional suction cup past the ostium of the LAA;
- d) allowing the self-expanding, radially torsional suction cup to self-expand within the LAA;
- e) attaching the aspiration catheter to an external suction device;
- f) activating the external suction device for transmission of negative pressure to the self-expanding, radially torsional suction cup;
- g) making suction contact between the self-expanding, radially torsional suction cup and the interior LAA wall;
- h) capturing the interior LAA wall within the self-expanding, radially torsional suction cup;
- i) withdrawing the aspiration catheter, thereby pulling the self-expanding, radially torsional suction cup and the LAA through the LAA ostium and into the left atrium to cause the LAA to assume an inverted hat configuration;

j) creating a torsional force at the torque handle to cause the self-expanding, radially torsional suction cup to radially collapse around, compress, and stabilize the LAA in the inverted hat configuration;

k) subsequently removing the torsional force created at the torque handle to allow the self-expanding, radially torsional suction cup to radially re-expand and controllably release the self-expanding, radially torsional suction cup from the inverted LAA; and l) deactivating the external suction device to release any remaining suction contact between the self-expanding, radially torsional suction cup and the interior LAA wall, thereby maintaining the LAA in the inverted hat configuration without the need to implant a closure device.

9. The method of claim 8, wherein the self-expanding, radially torsional suction cup comprises a braided nitinol mesh structure in the form of radial struts that connect to the distal end of the torqueable aspiration catheter shaft and are torsion-responsive to rotation of the torque handle to cause the radial contraction and progressive reduction in the diameter and length of the self-expanding, radially torsional suction cup.

10. The method of claim 8, including, prior to the step of withdrawing the aspiration catheter and pulling the LAA through the LAA ostium, the step of repositioning and recapturing the self-expanding, radially torsional suction cup onto the interior LAA wall to assure proper inversion of the LAA.

11. The method of claim 8, wherein the torqueable aspiration catheter shaft and the self-expanding, radially torsional suction cup are slidably fitted within a delivery sheath of the aspiration catheter when the torqueable aspiration catheter shaft and the self-expanding, radially torsional suction cup are being maneuvered through the patient's vasculature and heart.

* * * * *